United States Patent
Depfenhart et al.

(10) Patent No.: US 10,569,098 B2
(45) Date of Patent: Feb. 25, 2020

(54) THERAPY SYSTEM FOR TRANSCUTANEOUS IN-VIVO TISSUE ENGINEERING

(71) Applicant: Euvaira Biotechs (PTY) LTD, Centurion (ZA)

(72) Inventors: Markus Depfenhart, Hamburg (DE); Jörg Müller, Hamburg (DE)

(73) Assignee: Euvaira Biotechs (PTY) LTD, Centurion (ZA)

( * ) Notice: Subject to any disclaimer, the term of this patent is extended or adjusted under 35 U.S.C. 154(b) by 126 days.

(21) Appl. No.: 15/528,297

(22) PCT Filed: Nov. 20, 2015

(86) PCT No.: PCT/IB2015/059007
§ 371 (c)(1),
(2) Date: May 19, 2017

(87) PCT Pub. No.: WO2016/079717
PCT Pub. Date: May 26, 2016

(65) Prior Publication Data
US 2017/0348543 A1    Dec. 7, 2017

(30) Foreign Application Priority Data

Nov. 21, 2014    (DE) .......................... 10 2014 017 197

(51) Int. Cl.
*A61B 18/18* (2006.01)
*A61N 5/06* (2006.01)
(Continued)

(52) U.S. Cl.
CPC .......... *A61N 5/0616* (2013.01); *A61B 18/203* (2013.01); *A61N 5/062* (2013.01);
(Continued)

(58) Field of Classification Search
CPC .................. A61N 5/0616; A61N 5/062; A61N 2005/0626; A61N 2005/0642;
(Continued)

(56) References Cited

U.S. PATENT DOCUMENTS

2009/0069741 A1    3/2009    Altshuler et al.

FOREIGN PATENT DOCUMENTS

| EP | 2548617 A2 | 1/2013 |
| EP | 2745819 A1 | 6/2014 |

OTHER PUBLICATIONS

International Search Report and Written Opinion—International Application No. PCT/IB2015/059007.

*Primary Examiner* — Aaron F Roane
(74) *Attorney, Agent, or Firm* — Mintz Levin Cohn Ferris Glovsky and Popeo, P.C.; Peter F. Corless

(57) ABSTRACT

The present invention relates to a therapy system for the treatment of the skin and subdermis with light. The system comprises a NIR light source which produces light with a wavelength adapted to an absorption maximum for exciting molecular oxygen in aqueous solution; an image recognition unit for detecting papillary end arterioles and their x-y-z coordinates, wherein a respective depth underneath the skin surface is determined as the z-coordinate by an autofocus function; an optical system for the optical coupling of the light of the NIR light source and the pattern recognition unit to the skin, with a focussing unit to controllably position the light with at least one focus point in the skin; and a control unit to control the NIR light source, the image recognition unit, and the optical system.

18 Claims, 4 Drawing Sheets

(51) Int. Cl.
*A61B 18/20* (2006.01)
*A61B 18/00* (2006.01)
*A61N 5/067* (2006.01)

(52) U.S. Cl.
CPC ............ *A61B 2018/00452* (2013.01); *A61N 2005/067* (2013.01); *A61N 2005/0626* (2013.01); *A61N 2005/0642* (2013.01); *A61N 2005/0659* (2013.01); *A61N 2005/0666* (2013.01)

(58) Field of Classification Search
CPC .... A61N 2005/0659; A61N 2005/0666; A61N 2005/067; A61B 18/203; A61B 2018/00452
USPC .......................................................... 607/88
See application file for complete search history.

THERAPY SYSTEM FOR TRANSCUTANEOUS IN-VIVO TISSUE ENGINEERING

This application is a National Phase application filed under 35 U.S.C. § 371 of PCT International Application No. PCT/IB/2015/059007 with an International Filing Date of Nov. 20, 2015, which claims under 35 U.S.C. § 119(a) the benefit of German Application No. 10 2014 017 197.3, filed Nov. 21, 2014, the entire contents of which are incorporated herein by reference.

FIELD OF THE INVENTION

The present invention relates to a two-stage therapy system for the directed production of a collagen matrix in the skin and the subcutaneous tissue, based on a NIR light source or a NIR laser light source.

BACKGROUND OF THE INVENTION

DE102011052002284 describes a laser therapy system for the directed production of a collagen matrix in the human skin, which is based in the first instance on a treatment of the skin with a photo-sensitive agent in combination with UVA lights, thereby to specifically ensure a cross-linking of photo-chemical collagen. Secondly, with the described laser therapy system, by a focused IR laser light and at corresponding energies in the skin and without damaging the epidermis, lesions can be produced at the papillary end arterioles, by which the corpuscular blood constituents are released and as a result the body's own repair processes are stimulated. With the body's own repair processes, on the one hand destroyed tissue is broken down and on the other hand a reconstruction of the cells and of the extracellular matrix, e.g. the collagen tissue, is brought about, resulting in skin renewal.

Other processes to achieve collagen production in the skin operate, for example, according to the principle of percutaneous collagen induction, so-called "needling", whereby either by a purely mechanical needle roller/stamp, or by semi-fully automatic needling apparatuses, lesions are produced in the skin and at the dermal end arterioles, as a result of which corpuscular blood constituents, such as among others thrombocytes are released into the extravascular space where they decompose. As a result thereof growth factors, for example TGF β3, VEGF, EGF, are released. These promote the decomposition and remodelling of scars and the formation of directed collagen in the dermis, as a result of which the skin is regenerated or rejuvenated to a certain extent.

With the aforementioned treatment methods a perioperative topical treatment with vitamin A and vitamin C containing creams is advantageous. This topical treatment results in high local levels of vitamin A and vitamin C, which are important co-factors or coenzymes for the formation of collagen and elastin, are reached in a target region of the skin.

Other skin-renewal and collagen-forming methods are based on the use of so-called "Energy Devices", which for example consist of ablative, preferably fractionated laser systems, e.g. the fraxel laser®, or of radiofrequency devices such as the Thermage® device, or a combination of a radio frequency impulse and needle puncturing device such as the ePrime® device or the Ulthera® device, which is based on ultrasound.

WO 2008/089344 A2 (Neev) describes a device and a method for IR laser light application, with which several focused light beams with up to 10,000 focus points or spots can be produced and applied. Because the light beam bundles are focused with a specific focal length, the respective light beam bundles enter the skin with a first cross-sectional area and underneath the epidermis it is compacted to a focal point, so that in the focal point a much higher light or energy density is produced than at the first cross-sectional area. As a result thereof, the light density in the focal point is great enough to cause a light-induced reaction in the skin, whereas in the first cross-sectional area, during the entry of the focused light, the epidermis remains largely undamaged.

Described applications comprise, for example, a stimulation or killing off of hair roots, treatment of acne, tattoos, colour changes, tanning, eye treatment including a production of subcutaneous cavities.

WO 2008/001 284 A2 (Verhagen et al) describes a laser therapy system and a method for a skin treatment in the depth of the skin, which is based on laser induced optical breakdown (LIOB) by plasma formation. With a camera and a monitor depressions in the skin can be made visible, thereby to specifically produce underneath these a laser wound irritation. Repair processes are then said to fill the depressions with newly formed collagen. The stress vectors and Langer's lines are not taken into consideration.

WO 02/053 050 A1 (Altshuler et al.) describes a device and a method for a light-induced treatment in the depth of the skin, wherein the light source can be either a laser light source or also a non-coherent light source. With this several focused light beam bundles are produced simultaneously because the optic comprises a lens system with many, net-like arranged lenses, which are made integrally or non-integrally. The device furthermore comprises a cooling element for the skin, which can be either a skin contact plate, or the lens system itself.

U.S. Pat. No. 7,198,634 describes a laser therapy system for treating the skin, which comprises an infrared light source as well as a light source with violet or blue spectrum.

The aforementioned method of percutaneous collagen induction ("needling") is invasive, painful, fraught with a high infection risk, and inexact. The method according to WO 2008/089344 is not specific and exact in respect of collagen production. In addition, toxic UV-light is applied. The method according to DE102011052002284 is specifically controlled and effective, but toxic UV-light is applied which in addition to a low skin penetration depth only achieves an effect in conjunction with a photosensitizer. As a result thereof a treatment can take place in only one focus plane, which lies relatively superficially. The photosensitizer that is used requires, among others, a medicine product authorisation for use in the skin. In addition, during topical use of the photosensitizer the penetration depth and distribution in the skin cannot be managed or controlled. Furthermore, when using topical photosensitizers intolerance reactions (photo irritations) or allergic reactions (photoallergy) frequently occur (from Spielman, H. L., Müller et al. (2000). For additional laser-needling a second IR laser light source is required, which entails additional costs for the purchase of the further light source and the expensive optics. Also for a localisation of the end arterioles in the skin expensive, problem-prone and costly methods are proposed, such as OCT, fluorescence microscopy or fluorescence tomography. Except for the process described in DE102011052002284, whereby treatment can take place in only one focus plane, with all current, laser-based or other methods ("energy devices") an anatomically physiological reconfiguration or remodelling of the tissue of the skin is not taken into account.

The object of the invention is, therefore, in order to eliminate the disadvantages of the prior art, to provide a light therapy system for an anatomically physiological reconfiguration of the tissue of the skin and deeper tissue layers, in particular the extracellular matrix (among others collagen and elastin matrix) which emits as little as possible toxic UV-radiation and which can be used in an as simple, quick and precise manner as possible.

SUMMARY OF THE INVENTION

According to a first aspect of the present invention there is provided a system for the treatment of skin with underlying tissue layers with a first light, the system comprising:
  a) a NIR light source (1) which produces the first light with a first wavelength in the range of 532-1500 nm, wherein the first wavelength is adapted to an absorption maximum for exciting molecular oxygen in aqueous solution, and wherein a light pulse time and a light energy are controllable,
  b) an image recognition unit (2), which is coupled optically to the skin, comprising
  a second light source for illuminating the skin in use, a camera unit and a pattern recognition unit for recognition of the image,
  wherein a second light of the second light source is produced with a second wavelength such that the second light at least penetrates up to the papillary end arterioles of the papillary blood vessels of the skin, and that the end arterioles are recognisable at the skin surface by an increased absorption or reflection relative to the other tissue and are recorded by the camera unit,
  wherein the pattern recognition unit comprises a first pattern recognition to recognise the increased absorption or reflection by the end arterioles at the skin surface thereby to determine the x-y coordinates in a plane of the skin surface;
  an autofocus function to sharpen the focus in the depth perpendicular to the skin surface, wherein a respective depth of the respective end arterioles under the skin surface is determined by the autofocus function and a second pattern recognition,
  c) an optical system (3) for the optical coupling of the first light of the NIR light source (1) and the second emitted and reflected light of the image recognition unit (2) with the skin,
  comprising a light deflection unit and a focussing unit (3a) with an adapter plate (3b) as an interface to the skin,
  wherein the adapter plate (3b) is designed to rest on the skin;
  wherein the light deflection unit and the focussing unit (3a) are designed to position the first light controllably in a horizontal plane parallel to the adapter plate (3b) and in a depth underneath the adapter plate (3b) in the skin as at least one focus point (4), and to emit the second light of the image recognition unit (2) through the adapter plate (3b) and receive the reflected light;
  d) a control unit (5) for controlling the NIR light source (1), the image recognition unit (2) and the optical system (3), which is designed
  in that in a predetermined annular or hollow cylindrical area (14) and the previously determined x-y coordinates and in a depth area between the respective end arterioles and the skin surface it produces a plurality of focus points (4) with a respective first light energy which is designed to produce an oxygen excitation in the skin;
  in that it produces a focus point (4) on the previously determined x-y coordinate and in the depth of the respective end arterioles with a second light energy, which is predetermined such that it makes the respective end arterioles there permeable for corpuscular blood constituents.

Preferably the adapter plate (3b) is designed with an inner area (17a) for the light radiation and an adjoining outer area (17b) surrounding the inner area (17a), wherein the outer area (17b) projects beyond a treatment area of the skin to such an extent that the inner area (17a) is positioned at a distance from the skin when the outer area (17b) rests on the surrounding skin.

In one embodiment the pattern recognition unit of the image recognition unit (2) comprises a third pattern recognition to be able to recognise on the surface mound-like skin bumps, wherein corresponding coordinates of the skin bumps are determined;
wherein the pattern recognition unit comprises a fourth pattern recognition which determines the distances of the skin bumps relative to one another in a plane parallel to the skin and distinguishes a first area (16a) with skin bumps with a first average distance between the skin bumps and a second area (16b) with skin bumps with a second average distance between the skin bumps, and
wherein by the control unit in the second area (16b) a greater number of the light energies per surface unit is applied than in the first area (16a).

In one embodiment the pattern recognition unit of the image recognition unit (2) comprises a third pattern recognition for the detecting of superficial skin bumps, wherein corresponding coordinates of the skin bumps are determined, and
wherein the first pattern recognition for determining the x-y coordinates of the end arterioles takes into account the coordinates of the skin bumps, to achieve increased accuracy in the determination of the x-y coordinates.

Preferably the skin bumps are determined by a projection and detection of laser light and according to the line projection method and the triangulation method, and/or
wherein the projection of the laser light for producing lines on the skin, the height of which is measured according to the line projection method and triangulation method, in order to determine the skin bumps, is produced by another laser light than the first or the second light.

Preferably after detecting the skin bumps and accordingly the papilla, local densities of the skin bumps per a surface unit are calculated and displayed on a monitor (6), so as to indicate to the person giving the treatment prominent tensile stresses in the skin.

In a preferred embodiment the optical system (3) comprises a diffractive optical element (DOE) and/or a digital mirror device (DMD) and/or another kind of spatial light modulator, which is designed to produce from the first light at the same time a plurality of focussed light beam bundles with a corresponding plurality of focus points (4), wherein the plurality of the focus points lies in the annular or hollow cylindrical area (4), and wherein the DOE and/or the DMD and/or another kind of spatial light modulator can be shifted by the control unit (5) in such a way that the plurality of the focus points (4) lie around the predetermined x-y coordinates and in the depth in the depth area between the respective end arteriole and the skin surface.

Preferably the first light energies, the second light energy on the respective x-y coordinate is produced simultaneously by the DOE and/or the DMD and/or another kind of spatial light modulator.

In one embodiment the annular or hollow cylindrical area (14) has an outside diameter of 5-30 µm at a wall thickness of 3-8 µm, wherein only the area of the wall thickness is impacted with the first light energies.

Preferably, the first wavelength lies in a range of 532-940 nm or 1064-1500 nm, even more preferably the first wavelength lies at 532 nm, at 577 nm, at 760 nm, at 762 nm, at 765 nm, at 780 nm, at 810 nm, at 880 nm, at 900 nm, at 940 nm, at 1064 nm or at 1270 nm, or the first wavelength may be at 577-765 nm or 800-1064 nm to ensure simultaneously the wavelength for the oxygen excitation as well as a for the needling or laser-needling a sufficiently great light absorption for haemoglobin; and/or wherein the NIR light source (1) is a NIR laser light source.

Preferably, the second wavelength lies in the range of 450-560 nm and 577-765 nm; and/or wherein the second light is emitted with two or more light wavelength ranges and correspondingly detected by the camera unit.

In one embodiment the focussing unit (3*a*) is designed to let the first light come out of the adapter plate (3*b*) with such a focal length that an underlying upper skin layer, which lies above the focus point (4) is not damaged, and the light effect of the first and the second energies only acts on the skin in the focus point (4), or
wherein the focusing unit (3*a*) is designed to let the first light come out of the adapter plate (3*b*) with a focal length and an aperture such that the inlet area into the underlying skin is greater by at least a factor 30 or a factor of 3-1000 than the cross-sectional area in the focus point (4),
wherein the first light energies are produced in respective first focus points (4) and the second light energies in respective second focus points (4), wherein a diameter of the first focus points (4) is greater by a factor than another diameter of the second focus points (4) and wherein the factor is greater than 2.

Preferably, the NIR light source (1) and the optical system (3) are designed such that by a suitable control simultaneously a plurality of the first light energies is produced at various focus points (4) in the annular or hollow cylindrical area (14) for application.

Preferably, the image recognition unit (2) is further adapted to quantitatively determine a shifting of the adapter plate (3*b*) on the skin, wherein the control unit (5) is designed to carry out automatically the producing and application of the first and the second light energies in the areas which at first were still untreated.

Preferably the optical system (3) with its light beam deflection and focusing optics (3*a*) comprises at least one lens, a grin lens, a micro lens, a concave lens, a cylinder lens, a diffusing lens, a Fresnel lens, a liquid lens, a first lens system, a second lens system, a light conductor, a light conductor fibre bundle, a light adapter head or a combination thereof as hybrid system; and/or
the optical system (3) comprises a plurality of light beam deflection and focusing optics arranged therein, which are designed to simultaneously produce a corresponding plurality of focused light beam bundles and focus points (4) with corresponding light spots behind the adapter plate (3*b*) and in the skin.

In one embodiment the control unit (5) automatically produces the plurality of the first and the second light energies behind the adapter plate (3*b*) along a predefined light spot matrix, wherein the plurality of the first or second light energies are produced either simultaneously or sequentially after one another.

The camera unit may be a digital holography camera or a light field camera.

The therapy system of the present invention provides for a light or a laser therapy system, a forming of the extracellular matrix, essentially of collagen and elastin, in the skin and in the underlying tissue layers, because of their physiological texture can be produced by a light with a wavelength in the NIR-range, excluding toxic UV light. Also, in contrast to known methods, an additional photosensitizer agent is not required. Several tissue layers of different depths can be treated.

The therapy system comprises an image recognition unit which emits a second light and detects the reflections thereof from the skin. A second wavelength for the second light is advantageously chosen such that as a result thereof respective papillary end arterioles in the papilla of the skin can be properly recognised. The second wavelength is chosen such that an optimised contrast is brought about in the reflection of the papillary end arterioles in comparison to the other tissue. The skin is radiated here with the second wavelength and its reflections are recorded by a camera unit and evaluated by a pattern recognition unit. In this way the x-y coordinates of the respective end arterioles, and accordingly of the respective papilla, can be detected well by the pattern recognition unit. Since a depth, or the z-coordinate of the respective end arterioles in the skin, is determined by an autofocus mechanism, the design of the image recognition unit is simple and inexpensive. Through this type of a position determination of the end arterioles, expensive and complicated coherence tomographs can be dispensed with. As a result such therapy systems can be suited for home use at relatively low-cost.

Particularly advantageous of the image recognition unit is the speed of recognition of the end arterioles in an image of the camera unit, since the skin need only be radiated constantly with the second light to take an image with the camera unit, which can be evaluated in a short space of time by a threshold detection process, thereby to either detect the end arterioles as dark or as bright dot areas. The present image recognition unit operates much faster when compared with the computationally intensive coherence tomography process. This also clearly reduces the risk of an interim shifting between the detection and a therapeutic treatment by the first and the second light energies.

When the x-y-coordinates and the depth or z-coordinates of the end arterioles have been determined by the image recognition unit, then in a second step, focused first light in the NIR wavelength range of 532-1500 nm is applied around the respective x-y-z coordinates for the treatment. With this the first wavelength of the focused first light is predetermined such that the first wavelength is adapted to an absorption maximum for the stimulation of molecular oxygen in aqueous solution (see FIG. 8). As a result thereof an oxygen excitation is produced in the skin, which results in deamination of proteins of the extracellular matrix, such as collagen, elastin, proteoglycans and glycosaminoglycans (GAGs), which in the deaminated state results in an aldol condensation for a crosslinking. Toxic UV radiation can be completely dispensed with.

In a second step, or simultaneously, a control unit of the therapy system brings about a light or laser needling in that in the x-y-z coordinates of the respective end arterioles a second light energy is applied, which is predetermined in such a way as to make the end arterioles there permeable for corpuscular blood constituents.

Advantageously, the therapy system manages with only one light or laser-light source for the therapeutic first light, with which the respective first light energies are produced in a perimeter around the respective x-y-z coordinates and the second light energy is produced on the respective x-y-z coordinates.

Because an IR or NIR light is used, the IR or NIR light penetrates deeper into the skin and the underlying tissue layers than UV-light, and as a result thereof treatment in the deeper-seated tissue layers is made possible. Especially advantageous with this is also a treatment possibility in the depth of the skin in the area of the retaining ligaments.

Because by the image detection unit preferably skin bumps of the upper skin are topographically detected and during this the distances between them are determined, which refers to the distances of the apices of the respective skin bumps to one another, in a simple manner the distance between the underlying papilla can be determined. It is assumed here that the papilla that lie underneath the epidermis arch the epidermis accordingly and in this way produce a print of the papilla. By determining the distances between the skin bumps a further parameter is, therefore, provided for recognising the x-y coordinates of the papilla in a x-y plane parallel to the skin. Preferably the pattern recognition for determining the x-y coordinates of the papilla takes into account the positions of the skin bumps, so that the recognition of the x-y coordinates of the papilla becomes more accurate.

Preferred is an adapter plate, which constitutes the interface between the therapy system and the skin, equipped with a trough in relation to the skin, so that the skin does not come into direct contact with the adapter plate so that its surface will not be deformed by it.

In the determining of the skin bumps known line projection processes and triangulation processes are used. Because for the topographic survey of the skin preferably, in addition to the second light of the image recognition unit, a further light is used with a further wavelength, which differs from the second wavelength, the topographic surveys can take place at the same time as the determination of the depth of the respective end arterioles. This speeds up recognition processes and treatment.

Because the further wavelength in addition differs from the first wavelength, the topographic survey can take place quasi simultaneously with a therapeutic treatment with the first or the second light energies, as a result of which the risk of an interim shifting of the adapter plate in relation to the skin is clearly reduced.

Since preferably the skin bumps are determined, first areas with a smaller papilla distance and second areas with a larger papilla distance can be recognised. Assuming that the second areas represent a more expanded skin, it can be deduced that the second areas must be cross-linked with collagen and elastin to a greater extent than the first areas. This information is preferably evaluated by the control unit in that in the second areas a greater number of first energies is applied in the respective focus points compared to the first areas.

By determining the distances of the skin bumps relative to one another, assuming an identical slackening of the skin, it is possible to conclude a suspension of the skin caused by the retaining ligaments between bones and skin. By discriminating between the first and the second areas of the skin bumps, main stress vectors in the skin become discernible or can be made technically determinable. Since in the second areas outside the retaining ligaments the collagen structure must be restored in deeper skin layers, especially also here the treatment with NIR light is much more advantageous than that with UV-light because NIR light penetrates considerably deeper into the skin compared to higher frequency UV-light. Also conceivable under therapeutic use of the NIR light is a firming of the fatty tissue (cellulite) and/or a lipolysis by emulsification of the fatty tissue cells.

With respect to the first wavelength it is particularly advantageous to use a wavelength in the range of 532-940 nm, or 1064-1500 nm, to ensure simultaneously the wavelength for the oxygen excitation as well as for the needling or laser-needling and sufficiently great light absorption for haemoglobin. Particularly preferred wavelengths include 532 nm, 577 nm, 578 nm, 760 nm, 762 nm, 765 nm, 780 nm, 810 nm, 880 nm, 900 nm, 940 nm, 1064 nm and 1270 nm.

Preferably the optical system comprises a Diffractive Optical Element (DOE) and/or a Digital Mirror Device (DMD) and/or another kind of spatial light modulator, so as to simultaneously apply several focus points. The first light entering the optical system is divided into several focused light beam bundles, which each produce a focus point and are arranged such that they are applied around the x-y coordinates and in the depth of the end arterioles. With this the energy of the first light that enters the optical system is of course many times greater than in a single focus point. Advantageous here is a simultaneous application of focus points and a saving of time. The treatment can therefore take place many times quicker compared to a sequential addressing of a position and an only small first light energy.

Preferably the Diffractive Optical Element (DOE) and/or a Digital Mirror Device (DMD) and/or another kind of spatial light modulator is designed in such a way that the second light energy for the laser-needling is applied simultaneously in the x-y coordinates and in the depth of the end arterioles (z-coordinate). With this the Diffractive Optical Element (DOE) and/or the Digital Mirror Device (DMD) and/or another kind of spatial light modulator takes into account quantitatively the first light energies and the second light energy and the first light entering the optical system is divided accordingly.

Preferably the light source is a laser light source, which may also consist of a series of optically interconnected semiconductor lasers.

Preferably the image detection unit is designed to detect a shifting of the adapter plate on the skin, so as to be able to detect areas already treated by the therapy system and areas that still requires treatment. Advantageously the control unit evaluates the treated and not yet treated areas so that it automatically only treats the areas still to be treated with the light.

BRIEF DESCRIPTION OF THE DRAWINGS

The invention will now be described in more detail with reference to the following non-limiting embodiments and Figures in which.

DETAILED DESCRIPTION OF A PREFERRED EMBODIMENT

The present invention will now be described more fully hereinafter with reference to the accompanying figures, in which some of the embodiments of the invention are shown.

The invention as described hereinafter should not be construed to be limited to the specific embodiments disclosed, with slight modifications and other embodiments intended to be included within the scope of the invention. Although specific terms are employed herein, they are used in a generic and descriptive sense only and not for purposes of limitation.

As used throughout this specification and in the claims which follow, the singular forms "a", "an" and "the" include the plural form, unless the context clearly indicates otherwise.

The terminology and phraseology used herein is for the purpose of description and should not be regarded as limiting. The use of the terms "comprising", "containing", "having", "including", and variations thereof used herein, are meant to encompass the items listed thereafter and equivalents thereof as well as additional items.

Figure 1:
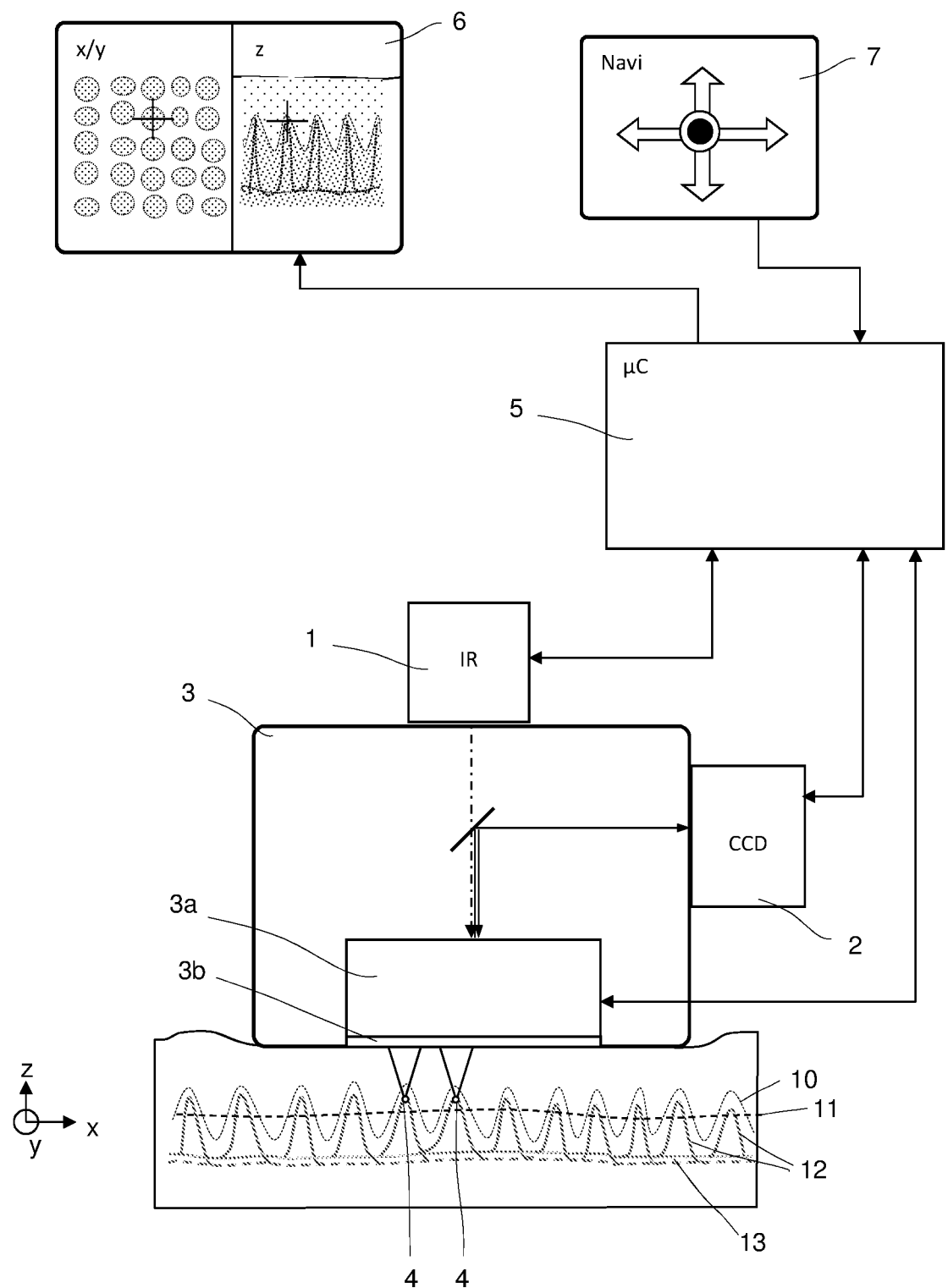
FIG. 1 shows a schematic illustration of a therapy system according to the present invention, comprising a NIR light source and an image recognition system with a second light source and a camera, which are coupled to skin by an optical system. A control unit controls the NIR light source and the image recognition system and in doing so reads data. A monitor displays image data of the camera and pattern recognition of the image recognition system. Two focus points are applied in a depth of the skin by a first light of the NIR light source.

FIG. 1 shows a schematic illustration of a preferred therapy system for treating a volume like area of the skin with light. It should be understood that the term "skin" is used to generally refer to human tissue which extends from the epidermis up to in a depth of the dermis and in underlying tissue layers. Light refers to a focused light which is produced by a NIR light source 1, passed through an optical system 3 and behind an adapter plate 3b of the optical system 3 is emitted at least as a part of the light with a focal length and a corresponding focus point 4. The therapy system is designed to position the focus point 4 or several focus points 4 precisely behind the adapter plate and thus apply correspondingly precise in the skin.

FIG. 1 shows the skin with a contour of the papilla 10 and the end arterioles 12, which are connected to the arterial and venous blood vessels 13. A collagen tissue area 11 is indicated by a broken line and sketched lying between the papilla 10.

The NIR light source produces the light with a first wavelength in an area of 532-1500 nm. The first wavelength is adapted to an absorption maximum for inducing molecular oxygen in aqueous solution. The light pulse time and light energy can be controlled by a control unit 5, which in accordance with the NIR light source and optical elements of the optical system 3, controls the beam deflection and/or shading. For clarification: In this step the wavelength range is already counted from 532 nm up to the NIR range, also when it is only red light.

Preferably the NIR light source 1 is a nano- or picosecond laser, which produces the first wavelength with a first intensity.

Alternatively, the NIR light source is a femtosecond laser, with a twice as long wavelength than the first wavelength, but by two light pulses following close on one another, produces the first wavelength.

Alternatively preferred is the NIR light source of a VIS-NIR light source for visible and near infrared light.

An image recognition unit 2 is in the therapy system coupled to the skin, both via the optical system 3 and the adapter plate 3b. The image recognition unit 2 comprises a second light source for illuminating the skin, a camera unit for detecting the second light reflected on and in the skin, and a pattern recognition unit in addition to the image recognition. With this a second light of the second light source with a second wavelength is produced in such a way that the second light penetrates at least up to the papillary end arterioles of the papillary blood vessels of the skin, so that the end arterioles are recognisable relative to the other tissue on the skin surface by an increased absorption or reflection, and can be recorded by the camera unit.

The pattern recognition unit of the image recognition unit 2 comprises a first pattern recognition to recognise the increased absorption or reflections by the end arterioles at the skin surface in an image of the camera unit, preferably either by dark or by bright areas in same. Recognition can take place here by a simple threshold value detection of the pixel intensities in the image. With this, by the first pattern recognition first of all respective x-y coordinates are determined in a plane parallel to the skin surface or to the adapter plate 3b. Preferably, the second light is projected on the skin as a dots array with a distance between the dots of 7-10 μm, so that less image information needs to be evaluated in the image of the camera unit, thereby saving time for the pattern recognition.

The third z-coordinate of the end arterioles, which represents a depth of the respective end arterioles under the skin surface, is determined by the pattern recognition unit by means of a second pattern recognition, which represents an autofocus function. The autofocus function sharpens a focus for the second light in the area of the end arterioles, wherein a sharpening is coupled to a respective depth or z-coordinate, which is determined by the second pattern recognition. To clarify: End arterioles always refer here to arterial and venous vessels in the papilla. Preferably the depth of the end arterioles is determined where the end arterioles have their reversal point and accordingly their highest point in relation to the surface of the skin. Preferably the autofocus function is ensured here by a piezo element, which is coupled to a lens system for the depth adaptation.

The optical system 3 serves for the optical coupling of the light of the NIR light source 1 and the second light emitted and reflected back from/to the pattern recognition unit, to the skin.

Figure 7:
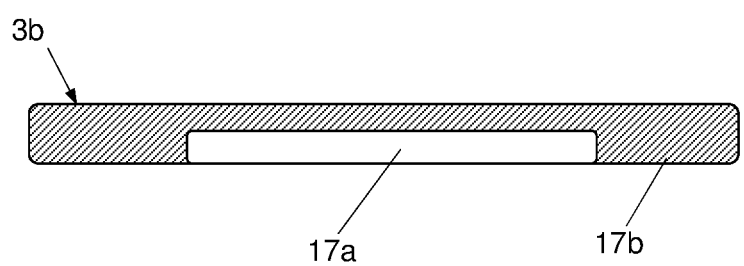
FIG. 7 shows a side-sectional view of an adapter plate of the optical system, which forms an interface between the therapy system and the skin.

The optical system 3 comprises a light deflection unit and a focussing unit 3a with the adapter plate 3b as the interface to the skin for the emitted light and the emitted and incoming second light. The adapter plate 3b is designed to rest on the skin. Preferably the adapter plate 3b is designed with an inner area 17a for the light irradiation and an adjoining outer area 17b surrounding the inner area 17a, wherein the outer area 17b sticks out from the treatment area of the skin to such an extent that the inner area 17a lies at a distance from the skin when the outer area 17b rests on the surrounding skin (see FIG. 7).

The light deflection unit and the focussing unit 3a are designed to position the light in a controlled manner in a horizontal x-y plane parallel to the adapter plate 3b and at a depth z perpendicular underneath the adapter plate 3b with at least one focus point 4. Preferably the focus point 4 has a diameter of 30-100 μm for the first light energies. For the second light energies the focus point 4 preferably has a diameter of 1.5-3 μm. The controlling thereof is ensured by the control unit 5. The light of the NIR light source is preferably focused with such a focal length and such an aperture that the light damages the epidermis as little as possible and deep in the skin in the focus point 4 at a correspondingly higher light energy density produces the desired therapeutic reaction by the light.

The second light of the image recognition unit 2, by the light deflection unit and the focussing unit 3a, also controlled by the adapter plate 3b, is emitted to the skin and the reflected portions thereof are received.

The control unit 5 serves to control the NIR light source 1, the image recognition unit 2 and the optical system 3. Preferably signals from these units may be received and if necessary converted and passed on to other units.

For example, the control unit 5 preferably controls a monitor 6, which shows images of the camera unit and preferably a pattern recognition of the image recognition unit 2. Preferably also an input unit 7 is connected to the control unit 5 so as to, for example, select a treatment area in the skin, feed in light control commands and/or other control parameters etc.

Figure 4:
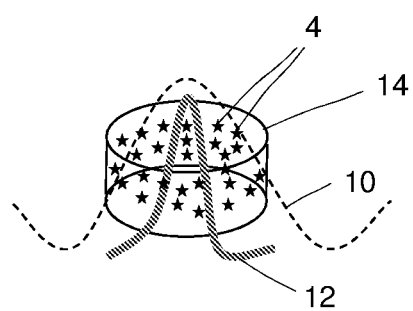
FIG. 4 shows a perspective view of an end arteriole, around which a hollow cylindrical body is arranged, in which focus points are applied with first energies.

Referring now to FIGS. 1 and 4, through the control unit 5, a plurality of focus points 4 is produced and acted on by a respective first light energy in a predetermined annular or hollow cylindrical area 14 around the previously determined x-y coordinates and in a depth area between the respective end arterioles and the surface of the skin. The NIR light source and the light deflection unit and the focussing unit 3a are controlled in such a way to reliably produce an oxygen excitation in the skin. The oxygen excitation brings about deamination of the side chains of proteins of the base substance (collagen, elastin, proteoglycans and glycosaminoglycans) which then in a deaminated state results in an aldol condensation for the cross-linking of, for example, collagen and elastin.

In addition, the control unit 5 produces and applies in at least one focus point 4 and the previously determined x-y-z coordinates, in the depth of the respective end arterioles, a second light energy. This second light energy is predetermined such that it makes the respective end arterioles there permeable for corpuscular blood constituents.

Under physiological conditions the enzyme lysyl oxidase (LOX) cross-links the collagen molecules in the extracellular space, after these have left the cell. Thus, for example, in the collagen molecule amino groups of specific amino acids are converted into aldehyde groups, which react either spontaneously with adjacent aldehyde groups in an aldol condensation or react with amino groups of amino acids under aldimine formation and form covalent crosslinks. This cross-linking is mainly responsible for the mechanical stability of collagen-containing tissues, and also for ensuring the physiological function. That is how the collagen acquires its natural strength and stability. With the Ehlers-Danlos syndrome there is a shortage of LOX, with keratoconus the LOX is reduced and in the case of keloids and scars increased. (From Kohlhaas, M: Collagen crosslinking with riboflavin and UV-light in the case of keratoconus, Ophthalmology 2008: 785-796).

Alternatively, a photo-oxidative crosslinking of the collagen with riboflavin can also take place, using UVA light. This method is known and commonly used in ophthalmology for treating the eye disease keratoconus. By the photo-oxidative crosslinking of the collagen with riboflavin and UVA light, the reduced mechanical corneal stability can be treated or the stability increased. This method was chosen because it acts in a locally limited manner, a short therapy time suffices and it leaves the transparency of the cornea unchanged. Riboflavin serves here as a photosensitizer to produce reactive oxygen species such as singlet oxygen Sport E. Raiskup-Wolf F., Pillunat L E. *Biophysical bases of collagen crosslinking*, Clin. Monthly Augenheilkunde (ophthalmology) 2008, 225, 131-127). When riboflavin absorbs energy from UV light, it is put into an excited state (excited singlet riboflavin1RF*). In an exchange mechanism the excited singlet riboflavin changes into excited triplet riboflavin (3RF*) (11). By interaction with triplet oxygen ($^3\Sigma_g^-$) singlet oxygen ($^1\Delta_g$ and $^1\Sigma_g^+$) is obtained, an oxygen radical which further interacts with the amino acids of the collagen.

This photochemical process modifies amino acids of the collagen. During the crosslinking on collagens active spots are formed along the molecular chain, which react with one another intermolecularly under aldimine formation and aldol condensation, and form covalent connections between the amino acids of collagen molecules. Also the formation of dityrosine from tyrosine was observed, by which the intermolecular and intramolecular crosslinking of the collagen molecules can come about. (From Koller T., Seller T.: Therapeutic crosslinking of the cornea by means of UVA and riboflavin (Clin. Monthly Augenheilkunde (Ophthalmology), 2007, 224: 700-706). Only where riboflavin is activated by UV light does a photochemical crosslinking effect occur or a photo-polymerisation take place, seeing that the singlet oxygen that occurs here has an only short life of 10-100μs and, therefore, can at the most diffuse a section of a few micrometres (From: Spörl E., Raiskup-Wolf F., Pillunat L. E.: Biophysical bases of collagen crosslinking. Clin. Monthly Augenheilkunde (Ophthalmology), 2008, 225 131-137).

Also when the riboflavin concentration is increased, more singlet oxygen is not necessarily formed, for riboflavin not only acts as a producer of singlet oxygen, but in high concentrations also as a radical catcher. Thus, at high concentrations equilibrium occurs between formation and destruction of singlet oxygen, i.e. a saturation process occurs (From: Spörl E., Raiskup-Wolf F., Pillunat L. E.: Biophysical bases of collagen crosslinking. Clin. Monthly Augenheilkunde (Ophthalmology), 2008, 225 131-137).

Explanation of terms: a system is called singlet (single) when the multiplicity is (2 S+1)=1. This is the case when the quantum number S of the total electron spin=0, i.e. when the spins of 2 electrons each compensate one another (S=(+½)+ (−½)=0).

The basic state of atomic oxygen is triplet-oxygen ($^3\Sigma_g^-$, two unpaired electrons, biradical), in the excited state singlet oxygen ($^1\Delta_g$ and $^1\Sigma_g^+$). Atomic, so-called nascent oxygen occurs at the moment of formation from chemical reactions.

In the case of singlet oxygen, an electrons pair can be absorbed directly into the 2pz-orbital, and this without having to change the spin of an electron, the activation energy is therefore smaller, the molecule accordingly more reactive (From: Bützer, 2014. Chemie Sauerstoff (chemistry oxygen), p. 4 et seq.).

The advantage of a light treatment with NIR light is a greater penetration depth than with UVA light and a greater independence of locally present riboflavin. Locally present riboflavin introduced by creams, for example, cannot be controlled and does not penetrate into the deeper lying skin layers, and not at all into the subcutis. As a result it displays an inhomogeneous distribution pattern.

It is envisaged that parts of the image recognition unit 2, such as for example the pattern recognition unit, can also form a part of the control unit.

Figure 2:
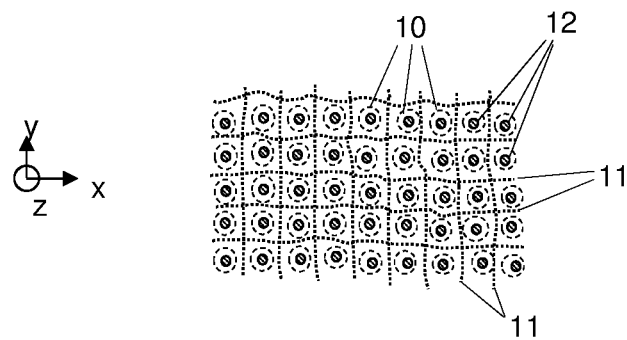
FIG. 2 shows a top view of skin structure with papilla and collagen fibres between. Dark points each represent end arterioles in papilla, which each have x-y coordinates. Sketched in a circle around the dark points are average papilla limits.

FIG. 2 is a top view onto the skin structure, illustrated schematically, wherein dark points represent the end arterioles 12 and dashed circles the papilla 10. Arranged between the papilla 10 are the collagen fibres.

Figure 3:
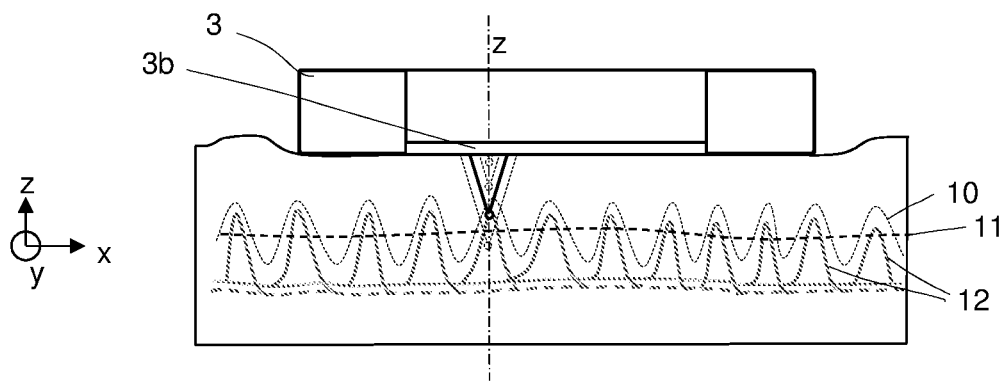
FIG. 3 shows a side view cross-section of the skin with the end arterioles in the papilla. In addition a focus point is shown, which is produced by the therapy system. The focus point can be set varied in a depth of the skin, so that during a sharpening the depth can be determined.

FIG. 3 in a side view shows in outline the therapy unit with the optical system 3, the adapter plate 3b and skin in cross-section that lies underneath same. Also shown is the cone-shaped focused light of the NIR light source 1 with the resultant focus point 4. Underneath and above the cone dash lines each indicate a cone-shaped focused light, which would occur when the autofocus function changes the focus point 4 in the depth along the z-axis.

FIG. 4 shows a perspective view of the end arteriole 12, around which in the predetermined annular or hollow cylindrical area 14 around the previously determined x-y-z coordinates of the particular end arteriole, the respective first light energy is applied to a multiplicity of focus points 4. The focus points are indicated by stars in FIG. 4.

Figure 5:
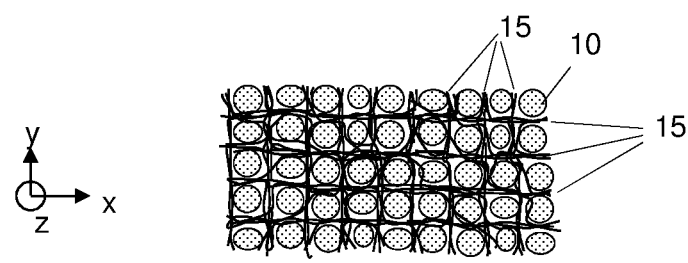
FIG. 5 shows a top view onto the skin papilla of the skin with between them additional cross-linked collagen fibres.

FIG. 5 shows a top view onto the skin the papilla 10, wherein by the treatment with the first light energies between the papilla 10 in addition cross-linked collagen fibres have formed.

Preferably the pattern recognition unit of the image recognition unit 2 has a third pattern recognition to recognise superficial mound-like skin bumps and determine their coordinates. The coordinates of the skim bumps relate to the apices of the skin bumps in an x-y plane parallel to the adapter plate 3b and to the skin. In addition, preferably also a height of the respective skin bumps orthogonally to the x-y plane is determined in a third pattern recognition.

Figure 6:
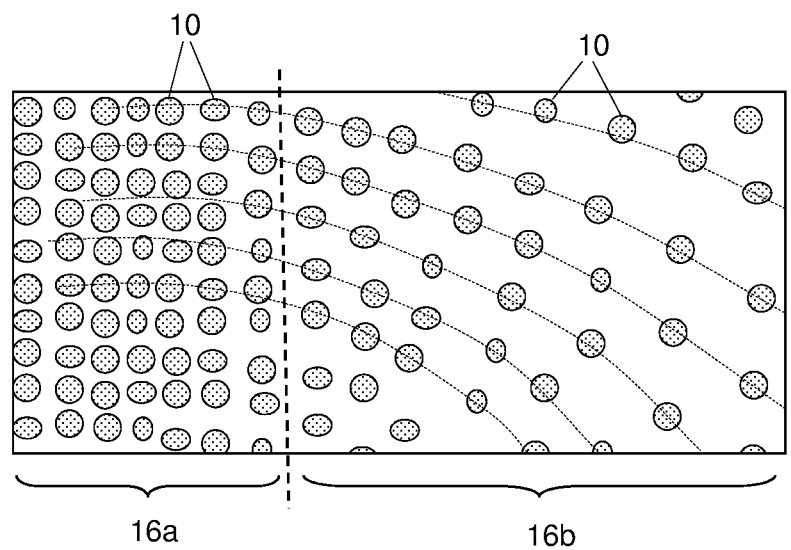
FIG. 6 shows a top view onto the skin papilla with different papilla distances, the papilla distances in a first area being smaller than in a second area.

Preferably the pattern recognition unit in addition comprises a fourth pattern recognition which determines distances between the skin bumps in the x-y plane. Referring to FIG. 6, preferably a first area 16a with skin bumps with a first average distance between the skin bumps, and a second area 16b with skin bumps with a second average distance between them are determined, wherein the second average distance is at least 10% greater than the first average distance. Knowing that the skin bumps are caused by the underlying papilla 10, and the lattice structure of the collagen fibres spread between the papilla, it is possible therefore to determine in a simple manner the distances of the papilla relative to one another. Furthermore, in this way information can be obtained about the shape and condition of a collagen matrix in the dermis and accordingly about a changing or stretching of the skin. In this way the main skin stress lines as well as the main stress vectors can also be determined. The control unit 5 is preferably designed to apply in the second area 16b a greater number of light energies per surface unit than in the first area.

FIG. 6 shows in a view from above onto the skin the first area 16a with smaller distances between the papilla 10 and the second area 16b with larger distances between the papilla 10. The expert will recognise from this that the retaining ligaments stop at the edge of the first area 16a to the second area 16b and a corresponding stress vector on the skin, which points down, can be assumed in the second area 16b. In this connection the control unit 5 is preferably designed such that the first and the second energies will be applied more intensely and at an increased rate in the second area 16b.

Preferably, the first pattern recognition to determine the x-y coordinates of the end arterioles 12 is designed to also take into account the coordinates of the skin bumps. This will ensure that the determination of the x-y coordinates of the end arterioles 12 takes place more accurately.

Preferably the skin bumps are determined by a projection and detection of laser light and the line projection method. Alternatively preferred, the skin bumps are determined by a projection and detection of laser light according to the triangulation or Scheimpflug method. Preferably the skin bumps are produced with a laser light other than the light of the NIR light source 1 and projected onto the skin as lines, to quasi at the same time detect the skin bumps and apply the first and/or second light energies targeted in the area of the skin bump in question. This ensures that in the event of a shifting of the adapter plate 3b relative to the skin, no larger deviations than necessary occur between a detection of the coordinates of the skin bumps and a therapeutic light application.

Preferably the optical system 3 comprises a Diffractive Optical Element (DOE) and/or a Digital Mirror Device (DMD) and/or another kind of spatial light modulator and is designed to produce from the first light a plurality of focused light beam bundles with a corresponding plurality of focus points 4. The plurality of the focus points lies in the annular or hollow cylindrical area 14. Preferably, the DOE and/or the DMD and/or another kind of spatial light modulator is shifted by the control unit 5 in such a way that the plurality of the focus points 4 lies around the predetermined x-y-z coordinates in the depth area between the respective end arterioles and the surface of the skin.

Preferably, the DOE and/or the DMD and/or another kind of spatial light modulator produce simultaneously with the first light energies the second light energy on the respective x-y-z coordinates.

Preferably, the annular or hollow cylindrical area 14 has an outside diameter of 5-30 µm at a wall thickness of 3-8 µm. With this the first light energies are applied to the area of the wall thickness.

Preferably the first wavelength lies in a range of 532-940 nm or 1064-1500 nm.

Preferably the first wavelength lies at 532 nm, at 577 nm, at 578 nm, at 630 nm, at 760 nm, at 762 nm, at 765 nm, at 780 nm, at 810 nm, at 880 nm, at 900 nm, at 940 nm, at 1064 nm, or at 1270 nm.

Particularly preferred, the first wavelength lies at 577, 578, 760, 762, 765, or at 1064 nm so as to ensure simultaneously the wavelength for the oxygen excitation as well as, for the needling or laser-needling, a sufficiently great light absorption for haemoglobin.

Figure 8:
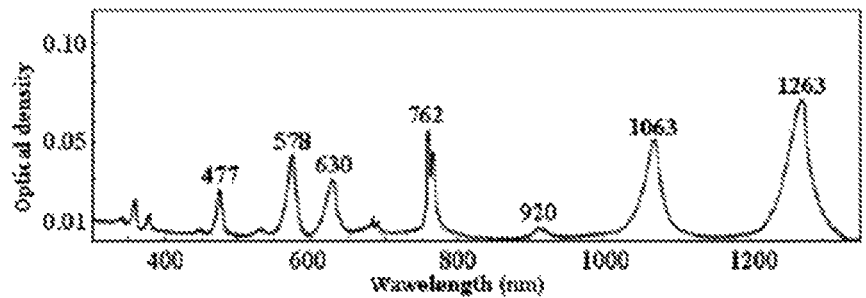
FIG. 8 shows a diagram of an absorption spectrum of molecular oxygen under high pressure over a wavelength range.
Figure 9:
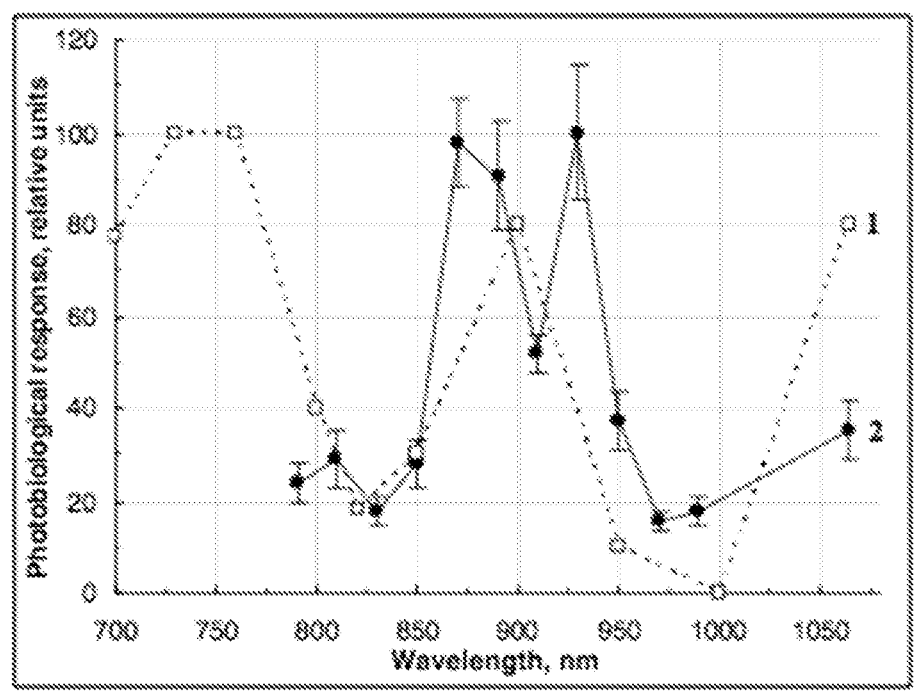
FIG. 9 shows a diagram of an action spectrum of light damage by laser radiation on individual ovary cells of hamsters over a wavelength range.

FIG. 8 shows a diagram of an absorption spectrum of molecular oxygen under high pressure over a wavelength range, and FIG. 9 shows a diagram which illustrates an action spectrum of light damage by laser radiation on ovary cells of hamsters over a wavelength range (From S. D. Zakharow, A. V. Ivanoc, Biophysics 50 (Suppl. 1), 64, 2005). Preferably the NIR light source 1 is a NIR laser light source. Preferably the NIR light source 1 also comprises two or more laser diodes, which together provide the light.

Preferably the second light of the image recognition unit 2 lies with its second wavelength in the range of 450-560 nm and 577-765 nm.

Preferably two or more light wavelength areas are radiated by the image recognition unit 2 and correspondingly detected by the camera unit.

Preferably the focusing unit 3a is designed to let the light of the NIR light source 1 come focused out of the adapter plate 3b with such a focal length that an underlying upper skin layer, which lies above the focus point 4, is not damaged and the light effect only occurs in or at the focus point (4) during the first or the second energy into the skin. Preferably the focusing unit 3a is designed such that the light of the NIR light source 1 comes out of the adapter plate 3b with a focal length and an aperture such that the inlet area into the underlying skin is greater by at least a factor 30 or a factor of 3-1000 than the cross-sectional area in the focus point 4.

Preferably the NIR light source 1 and the optical system 3 are designed so as to produce by a suitable control simultaneously a plurality of the first light energies for application at the various focus points 4 in the annular or hollow cylindrical area 14.

Preferably the first light energies are produced in respective first focus points (4) and the second light energies in respective second focus points (4), wherein a diameter of the first focus points (4) is greater by a factor than another diameter of the second focus points (4) and wherein the factor is greater than 2.

Preferably the image recognition unit 2 is furthermore designed to quantitatively determine a shifting of the adapter plate 3b on the skin, as is the case with known processes in PC mouses or other technical equipment. In this connection the control unit 5 is designed to carry out automatically the producing and application of the first and the second light energies in the areas which at first were still untreated.

Preferably the optical system 3 with its light beam deflection and focusing optics 3a comprises at least one lens, a grin lens, a micro lens, a concave lens, a cylinder lens, a diffusing lens, a Fresnel lens, a liquid lens, a first lens system, a second lens system, a light conductor, a light conductor fibre bundle, a light adapter head or a combination thereof as a hybrid system.

Preferably the optical system 3 comprises a plurality of light beam deflection and focusing optics arranged therein, which are designed to simultaneously produce a corresponding plurality of focused light beam bundles and focus points 4 with corresponding light spots behind the adapter plate 3b and in the skin.

Preferably the control unit 5 automatically produces the plurality of the first and the second light energies behind the adapter plate 3b along a predefined light spot matrix, wherein the plurality of the first or second light energies are produced either simultaneously or sequentially after one another.

Preferably the camera unit is a digital holography camera or a light field camera.

This above description of one of the illustrative embodiments of the invention is to indicate how the invention can be made and carried out. Those of ordinary skill in the art will know that various details may be modified thereby arriving at further embodiments, but that these embodiments will remain within the scope of the invention. In particular, also the various characteristics of the embodiments described above can be combined with one another, provided that they technically do not exclude one another.

The invention is not limited to the embodiment/s illustrated in the drawings. Accordingly, it should be understood that where features mentioned in the appended claims are followed by reference signs, such signs are included solely for the purpose of enhancing the intelligibility of the claims and are in no way limiting on the scope of the claims.

The invention claimed is:

1. A system for the treatment of skin and underlying tissue layers with a first light, the system comprising:
   a) a NIR light source which produces the first light with a first wavelength in the range of 532-1500 nm, and wherein a light pulse time and a light energy are controllable,
   b) an image recognition unit, which is coupled optically to the skin, comprising
   a second light source for illuminating the skin in use, a camera unit and a pattern recognition unit for recognition of the image,
   wherein a second light of the second light source is produced with a second wavelength such that the second light at least penetrates up to the papillary end arterioles of the papillary blood vessels of the skin, and that the end arterioles are recognisable at the skin surface by an increased absorption or reflection relative to the other tissue and are recorded by the camera unit,
   wherein the pattern recognition unit comprises a first pattern recognition to recognise the increased absorption or reflection by the end arterioles at the skin surface thereby to determine the x-y coordinates in a plane of the skin surface;
   an autofocus function to sharpen the focus in the depth perpendicular to the skin surface, wherein a respective depth of the respective end arterioles under the skin surface is determined by the autofocus function and a second pattern recognition,
   c) an optical system for the optical coupling of the first light of the NIR light source and the second emitted and reflected light of the image recognition unit with the skin,
   comprising a light deflection unit and a focussing unit with an adapter plate as an interface to the skin,
   wherein the adapter plate is designed to rest on the skin;
   wherein the light deflection unit and the focussing unit are designed to position the first light controllably in a horizontal plane parallel to the adapter plate and in a depth underneath the adapter plate in the skin as at least one focus point, and to emit the second light of the image recognition unit through the adapter plate and receive the reflected light;
   d) a control unit for controlling the NIR light source, the image recognition unit and the optical system, which is designed
   in that in a predetermined annular or hollow cylindrical area and the previously determined x-y coordinates and in a depth area between the respective end arterioles and the skin surface it produces a plurality of focus points with a respective first light energy which is designed to produce an oxygen excitation in the skin;

in that it produces a focus point on the previously determined x-y coordinate and in the depth of the respective end arterioles with a second light energy, which is predetermined such that it makes the respective end arterioles there permeable for corpuscular blood constituents.

2. The system according to claim 1, wherein the adapter plate is designed with an inner area for the light radiation and an adjoining outer area surrounding the inner area, wherein the outer area projects beyond a treatment area of the skin to such an extent that the inner area is positioned at a distance from the skin when the outer area rests on the surrounding skin.

3. The system according to claim 2, wherein the pattern recognition unit of the image recognition unit comprises a third pattern recognition to be able to recognise on the surface mound-like skin bumps, wherein corresponding coordinates of the skin bumps are determined;
wherein the pattern recognition unit comprises a fourth pattern recognition which determines the distances of the skin bumps relative to one another in a plane parallel to the skin and distinguishes a first area with skin bumps with a first average distance between the skin bumps and a second area with skin bumps with a second average distance between the skin bumps, and
wherein by the control unit in the second area a greater number of the light energies per surface unit is applied than in the first area.

4. The system according to claim 2, wherein the pattern recognition unit of the image recognition unit comprises a third pattern recognition for the detecting of superficial skin bumps, wherein corresponding coordinates of the skin bumps are determined, and
wherein the first pattern recognition for determining the x-y coordinates of the end arterioles takes into account the coordinates of the skin bumps, to achieve increased accuracy in the determination of the x-y coordinates.

5. The system according to claim 2, wherein the skin bumps are determined by a projection and detection of laser light and according to the line projection method and the triangulation method, and/or
wherein the projection of the laser light for producing lines on the skin, the height of which is measured according to the line projection method and triangulation method, in order to determine the skin bumps, is produced by another laser light than the first or the second light.

6. The system according to claim 3, wherein after detecting the skin bumps and accordingly the papilla, local densities of the skin bumps per a surface unit are calculated and displayed on a monitor, so as to indicate to the person giving the treatment prominent tensile stresses in the skin.

7. The system according to claim 1, wherein the optical system comprises a diffractive optical element (DOE) and/or a digital mirror device (DMD) and/or another kind of spatial light modulator, which is designed to produce from the first light at the same time a plurality of focused light beam bundles with a corresponding plurality of focus points, wherein the plurality of the focus points lies in the annular or hollow cylindrical area, and wherein the DOE and/or the DMD and/or another kind of spatial light modulator can be shifted by the control unit in such a way that the plurality of the focus points lie around the predetermined x-y coordinates and in the depth (z-coordinate) area between the respective end arteriole and the skin surface.

8. The system according to claim 7, wherein by the DOE and/or the DMD simultaneously and/or another kind of spatial light modulator with the first light energies the second light energy on the respective x-y coordinate is produced.

9. The system according to claim 1, wherein the annular or hollow cylindrical area has an outside diameter of 5-30 μm at a wall thickness of 3-8 μm, wherein only the area of the wall thickness is impacted with the first light energies.

10. The system according to claim 1, wherein the first wavelength lies in a range of 532-940 nm or 1064-1500 nm, or
wherein the first wavelength lies at 532 nm, at 577 nm, at 578 nm, at 760 nm, at 762 nm, at 765 nm, at 780 nm, at 810 nm, at 880 nm, at 900 nm, at 940 nm, at 1064 nm or at 1270 nm, or wherein the first wavelength lies at 577-765 nm or 800-1064 nm to ensure simultaneously the wavelength for the oxygen excitation as well as a for the needling or laser-needling a sufficiently great light absorption for haemoglobin; and/or
wherein the NIR light source is a NIR laser light source.

11. The system according to claim 1, wherein the second wavelength lies in the range of 450-560 nm or 561-765 nm; and/or
wherein the second light is emitted with two or more light wavelength ranges and correspondingly detected by the camera unit.

12. The system according to claim 1, wherein the focussing unit is designed to let the first light come out of the adapter plate with such a focal length that an underlying upper skin layer, which lies above the focus point is not damaged, and the light effect of the first and the second energies only acts on the skin in the focus point, or wherein the focusing unit is designed to let the first light come out of the adapter plate with a focal length and an aperture such that the inlet area into the underlying skin is greater by at least a factor 30 or a factor of 3-1000 than the cross-sectional area in the focus point, wherein the first light energies are produced in respective first focus points and the second light energies in respective second focus points, wherein a diameter of the first focus points is greater by a factor than another diameter of the second focus points and wherein the factor is greater than 2.

13. The system according to claim 1, wherein the NIR light source and the optical system are designed such that by a suitable control simultaneously a plurality of the first light energies is produced at various focus points in the annular or hollow cylindrical area for application.

14. The system according to claim 1, wherein the image recognition unit is further adapted to quantitatively determine a shifting of the adapter plate on the skin, wherein the control unit is designed to carry out automatically the producing and application of the first and the second light energies in the areas which at first were still untreated.

15. The system according to clam 1, wherein the optical system with its light beam deflection and focusing optics comprises at least one lens, a grin lens, a micro lens, a concave lens, a cylinder lens, a diffusing lens, a Fresnel lens, a liquid lens, a first lens system, a second lens system, a light conductor, a light conductor fibre bundle, a light adapter head or a combination thereof as hybrid system; and/or
the optical system comprises a plurality of light beam deflection and focusing optics arranged therein, which are designed to simultaneously produce a corresponding plurality of focused light beam bundles and focus points with corresponding light spots behind the adapter plate and in the skin.

16. The system according to claim 1, wherein the control unit automatically produces the plurality of the first and the second light energies behind the adapter plate along a predefined light spot matrix, wherein the plurality of the first or second light energies are produced either simultaneously or sequentially after one another.

17. The system according to claim 1, wherein the camera unit is a digital holography camera or a light field camera.

18. The system according to claim 1, wherein the first wavelength is adapted to an absorption maximum for exciting molecular oxygen in aqueous solution.

* * * * *